(12) United States Patent
Kennedy

(10) Patent No.: US 8,753,405 B2
(45) Date of Patent: Jun. 17, 2014

(54) HIP SURGERY NECK AND BALL ADJUSTMENT APPARATUS AND METHOD

(76) Inventor: Michael T. Kennedy, San Clemente, CA (US)

(*) Notice: Subject to any disclaimer, the term of this patent is extended or adjusted under 35 U.S.C. 154(b) by 254 days.

(21) Appl. No.: 13/506,144

(22) Filed: Mar. 30, 2012

(65) Prior Publication Data

US 2013/0261762 A1    Oct. 3, 2013

(51) Int. Cl.
*A61F 2/32* (2006.01)
(52) U.S. Cl.
USPC ............. 623/22.42; 623/22.43; 623/22.45
(58) Field of Classification Search
USPC .......................... 623/22.43, 22.45
See application file for complete search history.

(56) References Cited

U.S. PATENT DOCUMENTS 5,865,850 A * 2/1999 Matthews .................. 623/22.43

* cited by examiner

*Primary Examiner* — Thomas J Sweet
*Assistant Examiner* — Matthew Schall
(74) *Attorney, Agent, or Firm* — William W. Haefliger

(57) ABSTRACT

The method of accurately and correctly fitting and axially positioning at implantable ball to the neck trunnion of a hip replacement device, as during surgery, the ball adapted to be received in a socket, the ball having a bore, the method including the steps providing the neck trunnion with deformable metallic surface ribs, providing a deformable adapter and fitting the adapter over the ribs, providing a trial ball having a non-metallic bore, and including axially forcibly fitting that bore over the deformable adapter to deform the adapter without deforming the ribs, as the trial ball adjustingly arrives at selected axial position on the neck trunnion corresponding to correct position of the trial ball in the socket, and correspondingly subsequent correct axial positioning of the implantable ball on the neck trunnion.

9 Claims, 3 Drawing Sheets

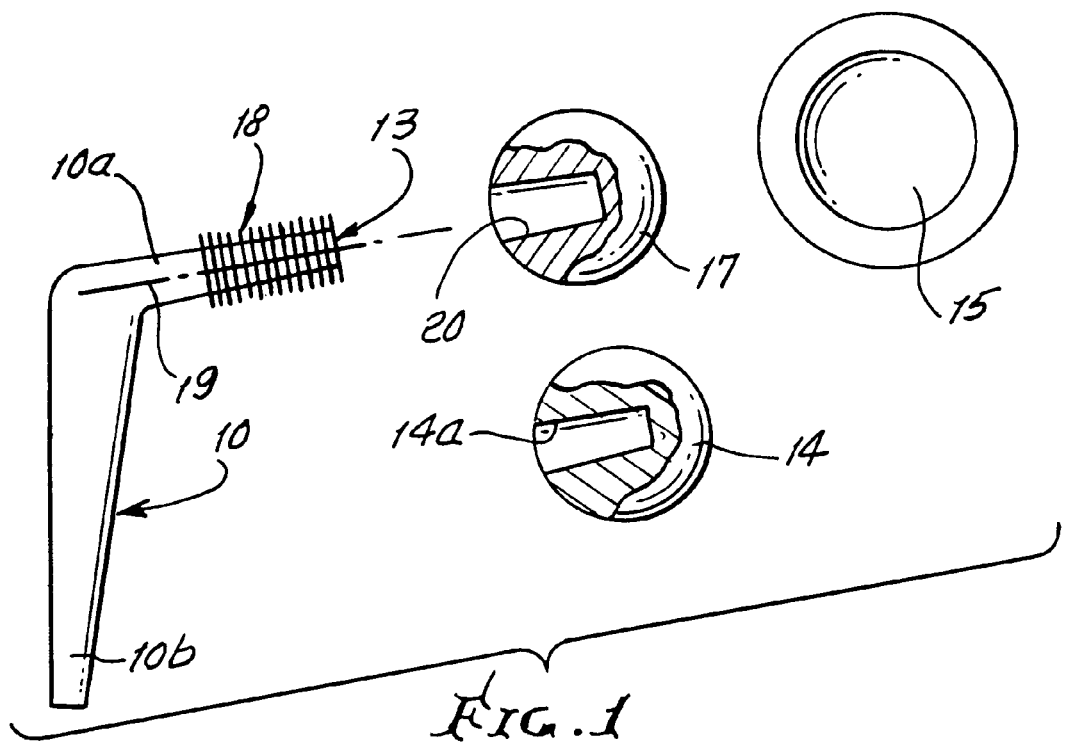
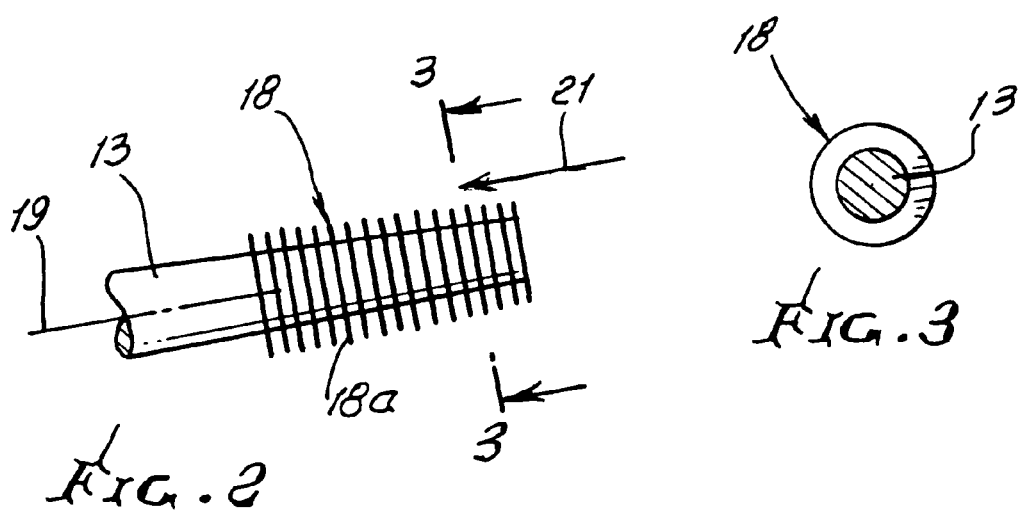

HIP SURGERY NECK AND BALL ADJUSTMENT APPARATUS AND METHOD

BACKGROUND OF THE INVENTION

This invention relates generally to human hip replacement, and more particularly to achieving more accurate leg positioning and joint stability, during surgery. The invention concerns implantable orthopedic prostheses for total hip replacement and, more particularly, a prosthesis which receives a modular head assembly selected for a desired leg length.

During such surgery, a replacement stem is employed and inserted lengthwise into a pathway in the femur. The stem carries an angularly extending i.e. offset neck trunnion, and a ball at the neck trunnion terminus, to be received into a socket defined by the joint. These components must be accurately relatively positioned to accommodate to each patient's particular femur and hip socket configuration, during surgery, which is time consuming and subject to adjustment problems and difficulties.

When the surgeon implants a definitive femoral prosthesis into the femur, the length and tension of the hip joint is assessed with a loose fitting trial head. The loose fit creates a situation of uncertain evaluation for the surgeon. The stem trunnion moves within the loose fitting trial head much like a piston does in a cylinder, and the surgeon is unable to make an absolute definitive decision as to which head length to implant permanently.

Manufacturers of hip stem prostheses utilize a cold weld (taper fit) of the head and stem trunnion that will unite the stem and the head as one solid unit. In the machining of the stem trunnion, fins are or ribs created that when impacted with the bore of the definitive head, (actual head to be implanted, either metal or ceramic) fold (deform) to create a locking mechanism between the stem and head. This trunnion, including its fins or ribs, are protected from deformity when trialing, by utilizing a loose fitting trial head that won't deform the fins. (the fins are therefore saved from for deforming by the actual head that will be implanted).

When the surgeon fits the femur with a trial stem and a trial head [with or without a trial neck] (some necks are built into the trial stems) the head forms a tight fit to the stem by means of a locking mechanism (a metal c-clip or rubber O-ring) so the surgeon can evaluate:

1) leg length
2) tightness
3) offset
4) dislocation
5) jump distance
6) other relative values The surgeon decides these relative values of head length with trials that provide an accurate assessment, because the head is captured and restricted from movement upon installation.

After the surgeon has placed (implanted) the definitive hip stem into the patient's femur it is customary to re-trial the head ball because the stem's final seating in the femoral envelope will change from that formed with the previously placed trial stem. The definitive stem can seat itself axially higher, lower, or at the same level as the trial stem, therefore necessitating the need to re-evaluate the head length.

The surgeon then places the same loose fitting trial head onto the definitive stem trunnion and re-evaluates relative values or positions, which are inaccurate because the stem trunnion simply moves axially lengthwise in the head trial. The surgeon wishes to see the head movement in the acetabular liner to evaluate dislocation, jump distance and other relative values necessary for proper head length determination (along the neck) (usual head length variables from −5 to 20 mm in increments et, −5, 2, 0, 1.5, 5, 8.5, 12, 15.5, 18, etc.). This varies by manufacturer.

There is need for apparatus and method to accurately and correctly fit and axially position the trial head ball, relative to it's supporting neck, during surgery.

SUMMARY OF THE INVENTION

It is a major object of the invention to provide an improved method of accurately and correctly fitting and axial positioning of a trial head ball to the tapered neck trunnion of a hip replacement device, a during surgery. As will be seen, the method includes the steps:

a) the tapered neck trunnion provided with deformable metallic surface ribs, b) providing a deformable adapter and trunnion protector and fitting the adapter over those ribs, or ridges, c) providing a trial ball having a non-metallic bore, and axially forcibly fitting that bore over the deformable adapter to deform the adapter without deforming the ribs, as the trial ball adjustingly arrive at selected and secure axial position on the neck trunnion, corresponding to correct position of the trial ball in the socket and correspondingly correct axial position of that ball on the neck, d) removing the trial ball from the socket and removing the trial ball and the adapter from the neck, e) and axially fitting the bore of the metallic or ceramic ball over and along said neck trunnion, to squeeze and deform the trunnion ribs as the metallic or ceramic ball forcibly arrives at the selected axial position on the neck trunnion, thereby to lock the metallic or ceramic ball to the neck trunnion, for correctly positioning reception in the socket.

Another object is to provide a purposeful trunnion (i.e. neck) protector that doubles as a spacer for trial heads and protects the trunnion from damage in total hip replacement surgery.

It is another object to provide a disposable or reusable film or shim device that recreates the tolerances of the definitive head and trunnion, so that when the surgeon trials (i.e. fits) the trial head and adapter on the stem, the trial head will stay in place for proper head length determination, along with other relative values.

The material of the adapter is typically made to the specification needed to allow the trial head to stay in its proper placement on the actual hip stem (definitive). This material must have the ability to be sterilized by various means and methods used in orthopedic implants. It must be biocompatible and have galvanic compatibility with hip trunnion materials.

Some examples of such material, but not all inclusive: Aluminum, Titanium, Cobalt, Chromium, Stainless Steel, Copper, Brass, Paper, Plastic, Rubber, Vinyl, Vanadium, Platinum, Gold, Silver, Teflon, UHMWPE (ultra high molecular weight polyethelene), Delrin, etc.

Such material can be made as formed for one time use (disposable), or as a reusable device.

Disposable examples include: Perforated Shrink bands, Aluminum foil bands; or any material that can be placed on the trunnion that is to be discarded prior to implanting the definitive metallic or ceramic head.

Reusable examples include: devices formed to the specifications of the manufactured trunion, and or neck, for repeated usage.

It is another object to provide for such adjusting of a trial ball endwise on a stem to establish the desired locking position of a subsequently fitted metallic or ceramic i.e. definitive ball, and without bending or compressive deformation of the trunnion rib peaks prior to fitting of the metallic or ceramic ball, wherein the adapter material is typically displaced into spaces between the ribs, for protection and retention of the trial ball (head).

A further object is to provide an adapter that either fits around the trunnion, or alternatively fits one side of the trunnion.

Yet another object is to provide a trial ball sized to fit a replacement hip socket, with the ball bore in pressing engagement with the side of the adapter, so that adapter material is displaced into spaces between the trunnion ribs, or fins, keeping firm retention of the trial ball, for accurate surgical assessment of all relevant values.

These and other objects and advantages of the invention, as well as the details of an illustrative embodiments, will be more fully understood from the following specification and drawings, in which:

DRAWING DESCRIPTION

FIG. 1 is an exploded side view of prosthesis neck trunnion, trial ball and socket elements;

FIG. 2 is an enlarged side view of the prosthesis neck trunnion, showing peripheral rib or form locations;

FIG. 3 is a section view taken on lines 3-3 of FIG. 2;

Figure 6:
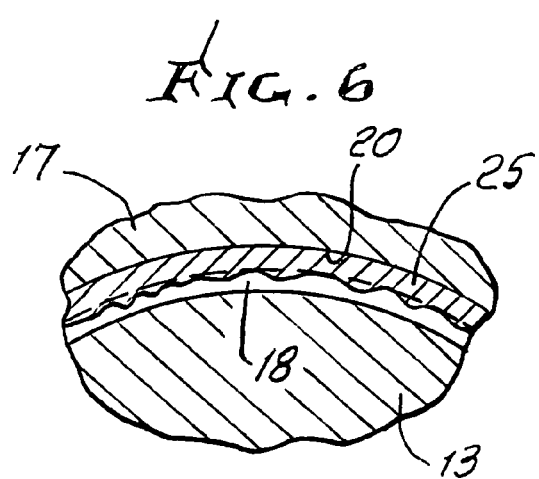
FIG. 6 is an enlarged sectional view taken on lines 6-6 of FIG. 4, showing adapter material deformed into spaces between trunnion ribs, or fins such ribs not being deformed.
Figure 6A:
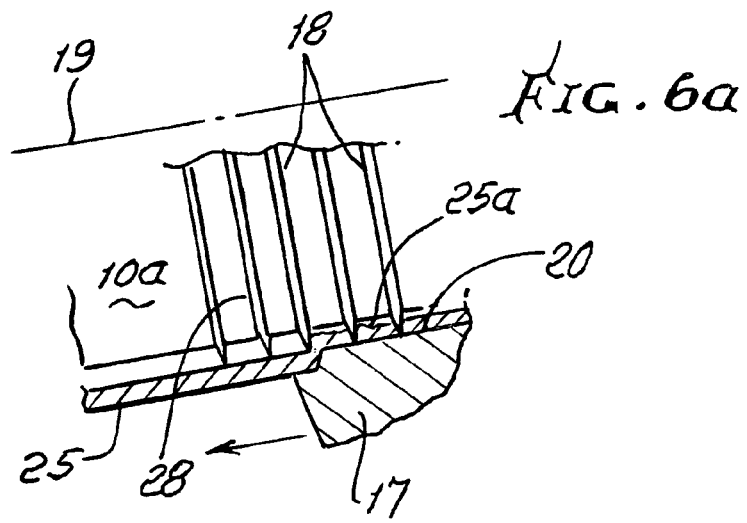
Figure 7:
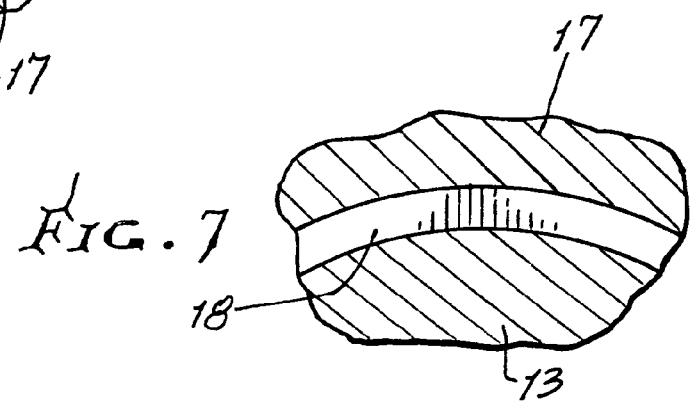
Figure 8:
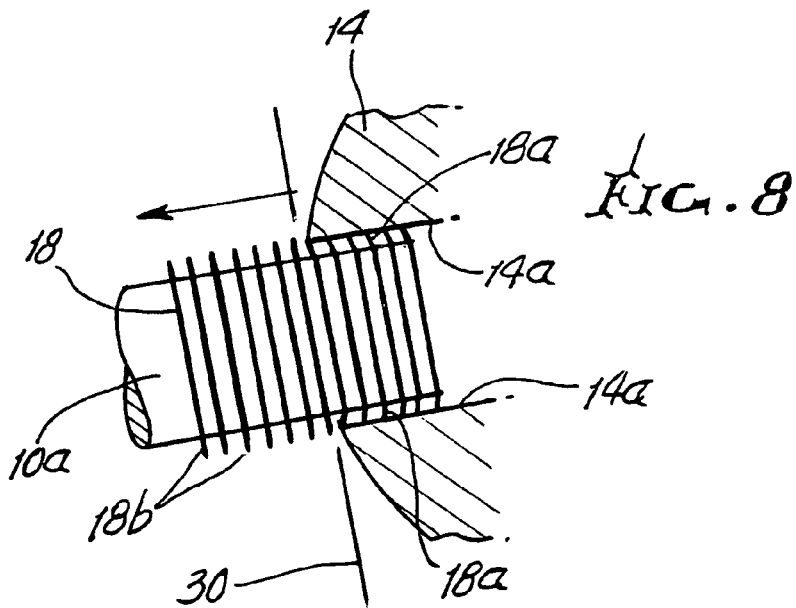

FIG. 6*a* is an enlarged schematic view to show deformation of the adapter to protrude into spaces between ribs;

FIG. 7 is a view like FIG. 6, but after removal of the adapter and trial ball from the neck, and after forcicle application of a definitive (for example ceramic or metallic) ball to the neck, deforming the fins or ribs to lock the definitive head in desired axial position established by use of the trial head; and FIG. 8 is a side view showing the definitive head in FIG. 7 locking position.

DETAILED DESCRIPTION

In FIG. 1, hip replacement components include a selected size elongated stem 10, having an angled upper end 10*a*, and a tapered lower end 10*b*, to fit endwise in a corresponding recess formed in a leg bone bore, i.e. femur. A neck 13 extends generally angularly from the upper end of the stem, to carry a definitive ball 14 that has a bore tapered at 14*a* to receive the end of the stem. A socket to receive the ball is shown at 15. Elements 10-15 are implantable at the time of hip replacement surgery. The definitive ball 14 is typically metallic or ceramic.

In accordance with the invention, a trial ball 17, typically non-metallic, such as plastic, is provided for trial assembly to the neck trunnion 13, prior to fitting and attaching the definitive ball to the neck, at a correct axial position, relative to the socket 15 and the stem 10.

The neck trunnion 13, typically metallic, has ridge-like ribs or fins 18, that extend about the trunnion axis 19, and that project circumferentially outwardly, as shown in enlarged FIGS. 2 and 3. The ribs are spaced generally axially, and extend circumferentially on the trunnion, which tapers endwise at a shallow angle, i.e. less than about 5°, as shown. The tips of such ribs become progressively deformed by forcibly engagement with the cylindrical bore 14*a* of the ball 14, and the surgeon needs to know the extent to which the ball 14 needs to be axially displaced in direction 21, on the trunnion, to arrive at correct position so that the stem 13 is correctly positioned laterally from the socket when the socket 15 receives the ball 14.

In this regard, the trial ball 17 may first be assembled onto the trunnion, but is loose, i.e. moves axially loosely, during fitting into the socket.

Figure 4:
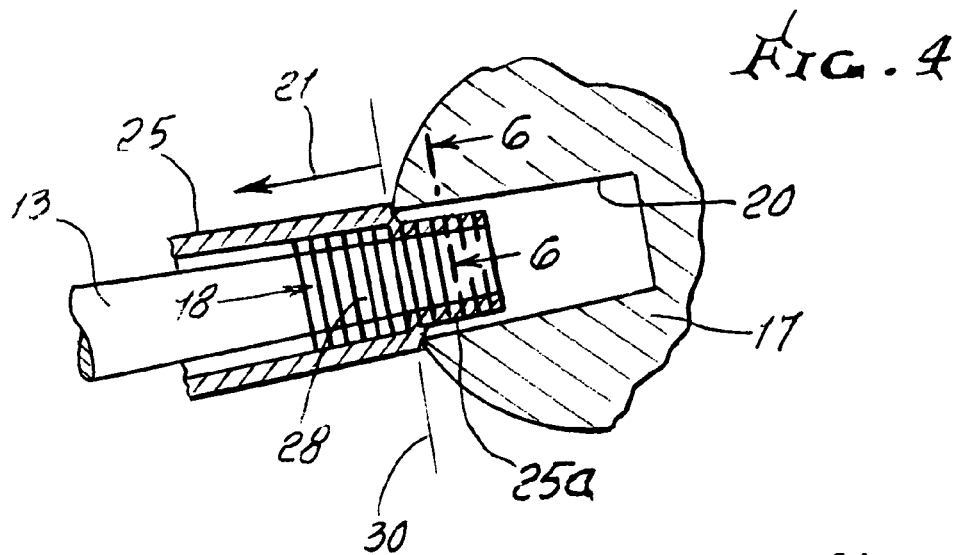
FIG. 4 is a further enlarged side view showing a sleeve adapter extending over the trunnion ribs, or fins and an assembled trial ball deforming the adapter, into spaces between ribs.
Figure 5:
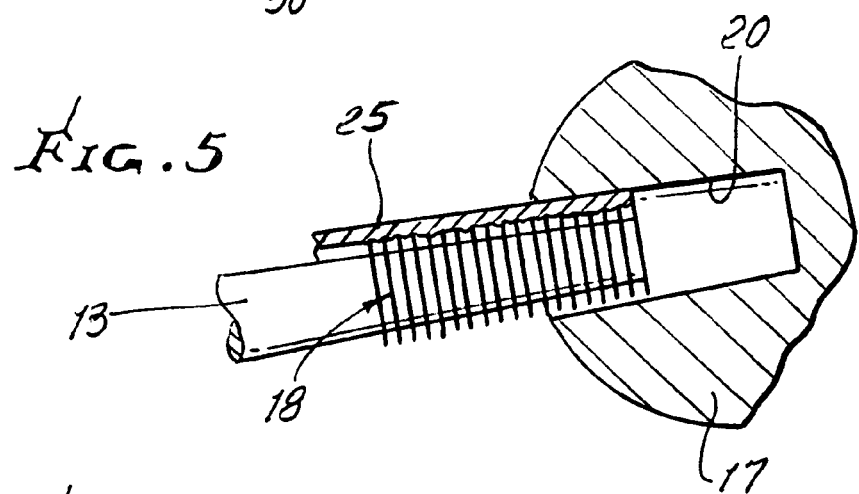
FIG. 5 is a view like FIG. 4, but showing another form of the adapter located at only one side of the trunnion.

To overcome such looseness, a deformable adapter 25 is provided, and fitted over the trunnion ribs, during surgery, prior to assembly of the trial ball over the ribs. The adapter is positioned over the ribs to be progressively deformed by the bore 20 of the trial ball, without ribs deformation. See FIG. 6*a* and deformed adapter material 25*a*. The trial ball is displaced endwise, to adjustingly arrive at selected axial position on the trunnion, correspondingly to correct position of the trial ball in the socket, which corresponds to the correct and desired axial position of subsequently assembled definitive ball in that socket. The trial ball holds its position relative to the trunnion due to pressured and frictional engagement with the adapter, which typically becomes deformed so that the adapter innermost extents 25*a* radially protrude into the spaces 28 between the undeformed ribs. See FIGS. 6 and 6*a*. Such maneuvering of the trial ball on the trunnion establishes the correct or "gauge" lengthwise position of the trial ball on the trunnion. That position may be recorded, as by measurement along the trunnion, or by marking the trunnion. See gauge (marker) line 30, in FIGS. 4 and 8. The ribs may extend with screw thread configuration, to allow "unthreading" of the deformable adapter, from the ribs.

Thereafter, the trial ball and adapter are removed from the neck, and the definitive ball 14 assembled to gauge position, accompanied by forcible deformation of the ribs and locking on to the trunnion taper by the bore 14*a* of the definitive ball, as the ball is impacted onto the taper of the stem's trunnion. It has a tighter fit as the hip ball slides further along the taper. The harder it is hit, the more it locks on.

FIG. 8 shows the bore of ball 14 depressing or bending the rib tips 18*a*, and line 30, relative to undepressed rib tips, at 18*b*. The adapter sleeve may consist of deformable metal mesh, such as copper or brass. A modified adapter extends at only one side of the tapered neck.

I claim:

1. A method of accurately and correctly fitting and axially positioning an implantable ball to the neck trunnion of a hip replacement device, as during surgery, the ball adapted to be received in a socket, the ball having a bore, that method including the steps:

a) said neck trunnion provided with deformable metallic surface ribs, defining ridges, extending with screw thread configuration about the neck trunnion, b) providing a deformable adapter and fitting the adapter over said ribs, c) providing a trial ball having a non-metallic bore, and axially forcibly fitting that bore over the deformable adapter to deform the adapter into spaces formed between the ribs, without deforming said ribs, as the trial ball adjustingly arrives at selected axial position on the neck corresponding to correct position of the trial ball in the socket, and correspondingly correct axial position of the implantable ball on the neck, the adapter being rotated to unscrew from the ribs and from said spaces between the ribs, d) removing the trial ball and the adapter from the neck trunnion, the adapter being rotated to unscrew from the ribs and from said spaces between the ribs, e) and axially fitting said bore of the implantable ball over and along said neck trunnion to squeeze and deform said ribs as the implantable ball forcibly arrives at said selected axial position on the neck trunnion, thereby to lock the implantable ball to the neck, for correctly positioning reception in the socket.

2. The method of claim 1 wherein the trial ball is adjusted on and endwise of the neck trunnion, to establish said correct position, without bending said ribs, but to displace adapter material into retention by the ribs.

3. The method of claim 1 wherein the adapter has sleeve configuration.

4. The method of claim 1 wherein the adapter is confined at one side of the neck trunnion during said e) step.

5. The method of claim 2 wherein the adapter has thin sleeve configuration to extend about the neck.

6. The method of claim 2 wherein the adapter remains removed from the neck during said e) step.

7. The method of claim 2 wherein the trial ball is sized to fit a replacement hip socket, with said trial ball bore pressurally engaging the adapter to hold the trial ball in axial position on the neck.

8. The method of claim 1 wherein the adapter is provided in the form of deformable metal mesh.

9. The method of claim 8 wherein the adapter is provided to have deformability greater than the deformability of said ribs, whereby adapter material is squeezed by the trial ball into spaces formed between the ribs.

\* \* \* \* \*